United States Patent [19]

Igich

[11] 4,025,590
[45] May 24, 1977

[54] SELF-SEALING HUMIDIFIER FOR INHALATION THERAPY

[76] Inventor: Victor Igich, 2022 44th Ave., Gulfport, Miss. 39501

[22] Filed: June 10, 1976

[21] Appl. No.: 694,624

[52] U.S. Cl. .............................. 261/122; 128/186; 220/22; 261/DIG. 65

[51] Int. Cl.² ................................. A61M 15/00

[58] Field of Search ............ 215/259, 261; 220/22, 220/209, 229; 128/186–192; 261/DIG. 65, 122, 124

[56] References Cited

UNITED STATES PATENTS

| | | | |
|---|---|---|---|
| 2,771,320 | 11/1956 | Korwin | 261/124 |
| 3,682,168 | 8/1972 | Deaton | 261/DIG. 65 |
| 3,807,713 | 4/1974 | Cornett et al. | 261/DIG. 65 |
| 3,892,235 | 7/1975 | Van Amerongen et al. | 261/DIG. 65 |

FOREIGN PATENTS OR APPLICATIONS

| | | | |
|---|---|---|---|
| 315,777 | 7/1929 | United Kingdom | 128/186 |

Primary Examiner—Tim R. Miles
Assistant Examiner—Gregory N. Clements
Attorney, Agent, or Firm—James B. Lake, Jr.

[57] ABSTRACT

A disposable, inhalation-therapy, container in which a chamber for liquid is defined between the sides, top and bottom of the container by transverse upper and lower, flexible, multi-slitted partitions, spaced from the top and bottom of the container. The partitions are porous when flexed by inhalation gas pressure and impervious when not so flexed. Inhalation gas under pressure is introduced into the space between the container bottom and the lower partition and flexes it to porosity, the gas bubbling through the liquid chamber is silenced and slowed by the upper partition as it is flexed into porosity by the gas pressure to better humidify the escaping gas for inhalation. When the therapy ceases, inhalation gas pressure is shut-off and the sterile liquid is resealed by the unflexed partitions in the liquid chamber.

4 Claims, 4 Drawing Figures

SELF-SEALING HUMIDIFIER FOR INHALATION THERAPY

BACKGROUND OF THE INVENTION

The invention relates to humidifiers for use in inhalation gas therapy, and more particularly to humidifiers in which aseptic conditions can be maintained for sterile reuses thereof.

Sterile liquid humidifiers are old in the art, gas entrance and exit being sealed until just before use. The seals are then broken, and no provision made for resealing for subsequent sterile uses.

SUMMARY OF THE INVENTION

It is an object of the invention to provide a humidifier for use in inhalation gas therapy that has a self-sealing liquid chamber for humidification that is porous when subjected to inhalation gas pressure and impervious when not.

Another object of the invention is to lower the noise level of the operating humidifier for the benefit of easily disturbed users thereof.

A further object of the invention is to provide a humidifier of greater efficiency than is presently available.

DETAILED DESCRIPTION OF THE ILLUSTRATED EMBODIMENTS OF THE INVENTION

Figure 1:
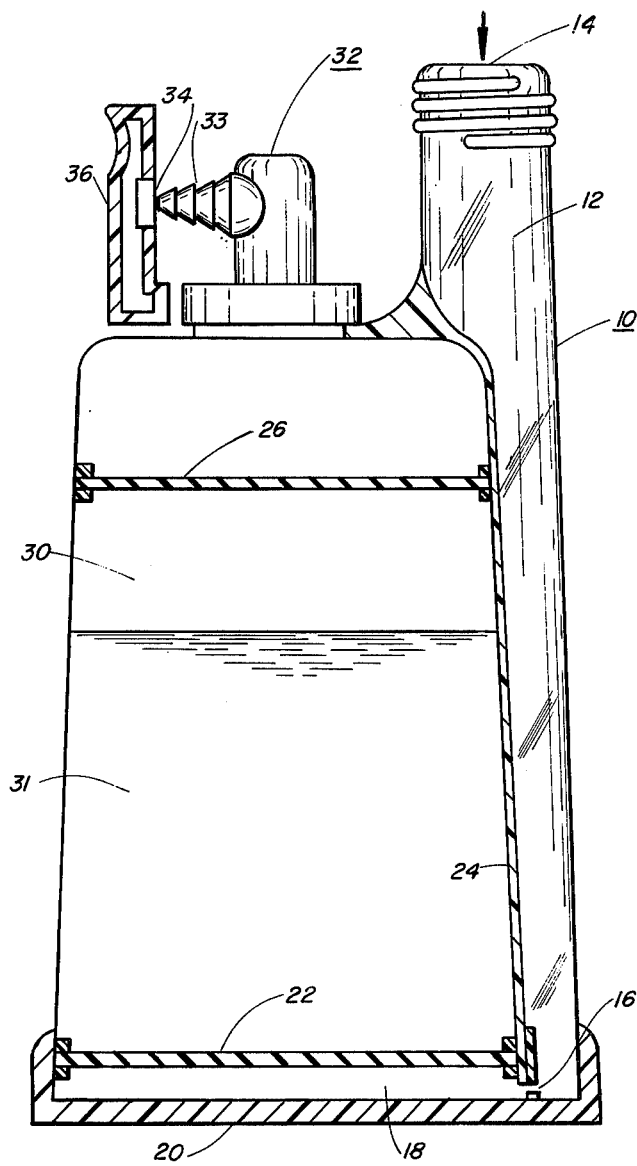
FIG. 1 is a side view of the invention.

Referring to FIG. 1, an inhalation-therapy container 10 comprises sides 11, an interior duct 12 that forms a part of said sides 11 and is adapted at an upper end 14 to be attached to an inhalation gas tank (not shown) for the entrance of gas to the container, A lower end 16 of said duct 12 opens into a double bottom 18 defined between a base 20 of said container and a flexible lower partition 22 that extends in sealing attachment between an inner side 24 of duct 12 and sides 11 of the container. A flexible upper partition 22 is spaced above and parallel to lower partition 22 and defines therewith and sides 11 and 24 a liquid chamber 30 that is partially filled as shown in FIG. 1 with sterile liquid 31. A top 32, spaced above upper partition 26, closes container 10 and defines an opening 33 in which is mounted an inhalation gas outlet 34 for humidified inhalation gas that has passed through liquid chamber 30 and sterile liquid 31 therein. Outlet 34 is closed until initial use by a break-to-open seal 36.

Figure 3:
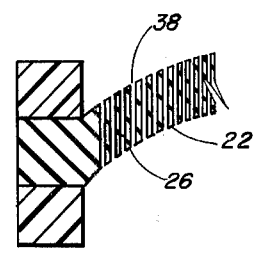
FIG. 3 is an enlarged cross-section of a partition flexed by inhalation gas pressure.
Figure 4:
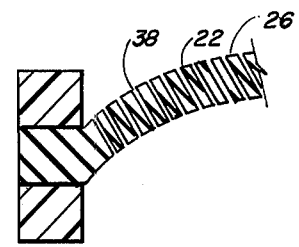
FIG. 4 is a second specie of FIG. 3.

Referring to FIGS. 3 and 4, the upper and lower partitions 26 and 22 are slitted with a plurality of tiny slits 38 that extend through said partitions and that may be normal or slanted to the parallel planes of the partitions, the slits being normally closed. When inhalation gas is admitted to the container, tha partitions are flexed to open by the gas pressure and the gas passes through steril liquid 31 in minute bubbles that ensure silent and efficient humidification of the gas. When therapy is ended and inhalation gas shut off, partitions 22 and 26 return to unflexed and closed slit condition, thereby sealing liquid chamber 30 and sterile liquid 31 from contamination through entrance 14 and exit 34.

Figure 2:
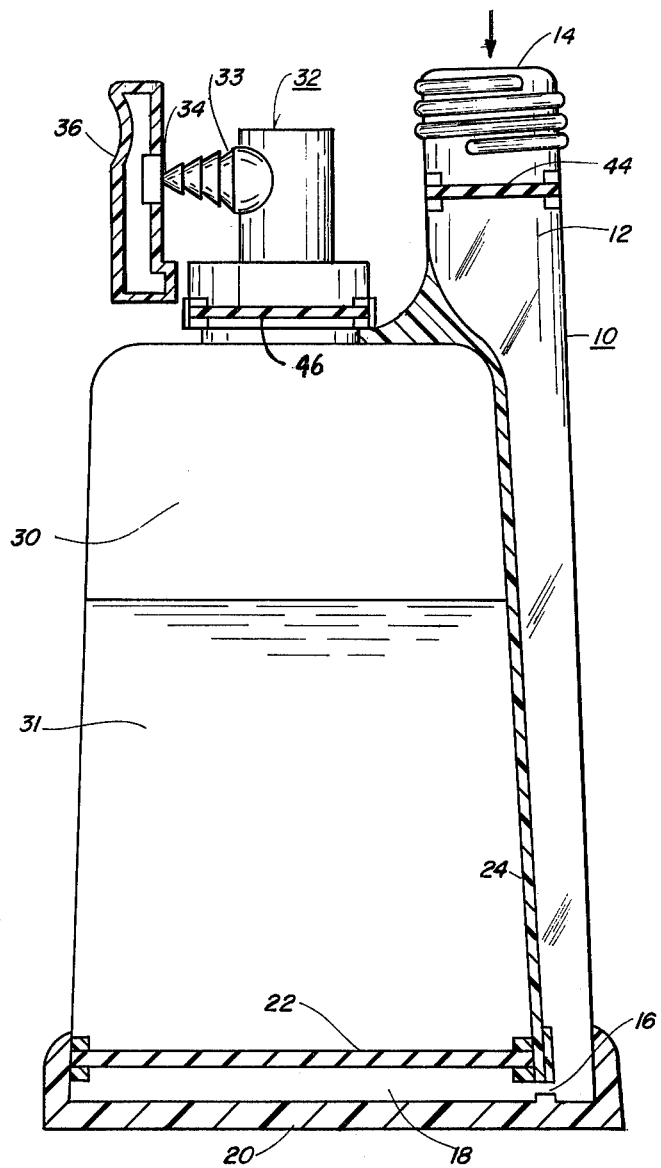
FIG. 2 is a second specie of FIG. 1.

Referring to FIG. 2, an additional partition 44 can be mounted just below entrance 14, and a partition 46 mounted in exit 34 in lieu of partition 26, in a second specie of the invention. These partitions 44 and 46 are slitted similarly to partitions 22 and 26.

What is claimed:

1. Self-sealing humidifier for inhalation therapy and adapted to connect with an inhalation gas cyclinder, comprises:
   a. container having a top, bottom, and sides with a vertical interior duct for directing inhalation gas to the bottom thereof;
   b. a pair of flexible partitions, horizontally fixed and vertically spaced apart in said container for defining a top space, a double bottom, and a liquid chamber therebetween, said partitions having a multiplicity of minute slits adapted to remain closed in a normal absence of inhalation gas pressure, thereby sealing said fluid chamber when said humidifier is not in use; and
   c. sterile liquid partially filling said fluid chamber and retained therein when in use by the passage of tiny gas bubbles continuously therethrough and out silently and humidified for inhalation therapy.

2. Self-sealing humidifier as described in claim 1 wherein said partitions are slitted normal to the flow of gas therethrough.

3. Self-sealing humidifier as described in claim 1 wherein said partitions are slitted at an angle to the flow of gas therethrough.

4. Self-sealing humidifier as described in claim 1 whereby an additional partition, similarly slitted is fixed in said duct, and the partition defining said top space is fixed in the top of said container, thereby sealing said container from outside contamination.

* * * * *